United States Patent
Shantilal Patel et al.

(10) Patent No.: US 7,550,605 B2
(45) Date of Patent: Jun. 23, 2009

(54) PROCESS FOR PREPARATION OF AN ANITDEPRESSANT COMPOUND

(75) Inventors: Kartik Shantilal Patel, Baroda (IN); Nischal Vinodbhai Patel, Baroda (IN); Rajeev Budhdev Rehani, Baroda (IN); Rajamannar Thennati, Baroda (IN)

(73) Assignee: Sun Pharmaceutical Industries Ltd., Mumbai (IN)

( * ) Notice: Subject to any disclaimer, the term of this patent is extended or adjusted under 35 U.S.C. 154(b) by 0 days.

(21) Appl. No.: 11/659,230

(22) PCT Filed: Aug. 5, 2005

(86) PCT No.: PCT/IN2005/000263

§ 371 (c)(1),
(2), (4) Date: Feb. 2, 2007

(87) PCT Pub. No.: WO2006/027798

PCT Pub. Date: Mar. 16, 2006

(65) Prior Publication Data

US 2007/0191616 A1  Aug. 16, 2007

(30) Foreign Application Priority Data

Aug. 5, 2004  (IN) .................. 846/MUM/2004
Feb. 14, 2005  (IN) .................. 159/MUM/2005

(51) Int. Cl.
C07D 333/16 (2006.01)
(52) U.S. Cl. ..................... 549/78
(58) Field of Classification Search ............... 549/78
See application file for complete search history.

(56) References Cited

U.S. PATENT DOCUMENTS 5,023,269 A * 6/1991 Robertson et al. ......... 514/438

FOREIGN PATENT DOCUMENTS

WO  056795  * 7/2004

* cited by examiner

*Primary Examiner*—Taofiq A Solola
(74) *Attorney, Agent, or Firm*—Sughrue Mion, PLLC

(57) ABSTRACT

The present invention provides optically pure (S)-(+)-N-methyl-3-(1-naphthaleneoxy)-3-(2-thienyl)propanamine, a compound of formula (I), and optically pure (S)-isomer of compound of formula 4, wherein $R^1$ and $R^2$ both are methyl or $R^1$ is methyl and $R^2$ is benzyl or substituted benzyl group and process for preparation thereof. Formula (I) and (IV). In another aspect the present invention provides a process for preparation of an acid addition salt of compound of formula (I).

12 Claims, No Drawings

PROCESS FOR PREPARATION OF AN ANITDEPRESSANT COMPOUND

The present invention provides (S)-(+)-N-methyl-3-(1-naphthalenyloxy)-3-(2-thienyl)propanamine, a compound of formula 1, and acid addition salt thereof in high optical purity and a process for preparation thereof.

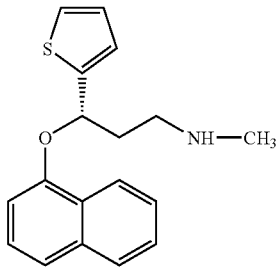

Formula 1

Duloxetine is the INN for the hydrochloride salt of (S)-(+)-N-methyl-3-(1-naphthalenyloxy)-3-(2-thienyl)propanamine, a pharmaceutical approved for treatment as an antidepressant.

Particularly the present invention provides a process for preparation of (S)-(+)-N-methyl-3-(1-naphthalenyloxy)-3-(2-thienyl)propanamine, a compound of formula 1, comprising the steps of:

a) reacting a mixture of R and S enantiomers of compound of formula 4,

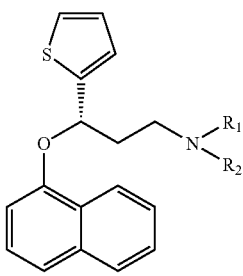

Formula 4 with Di-para-toluoyl-L-tartaric acid to precipitate the salt of (S)-isomer of the compound of formula 4 with Di-para-toluoyl-L-tartaric acid; wherein $R_1$ and $R_2$ both are methyl or $R_1$ is methyl and $R_2$ is benzyl or substituted benzyl group, and b) converting the said precipitated salt to the (S)-isomer of the compound of formula 4.

The present invention particularly provides (S)-isomer of intermediate compounds like (S)-(+)-N,N-dimethyl-3-(1-naphthalenyloxy)-3-(2-thienyl)propanamine, a compound of formula 4, wherein $R_1$ and $R_2$ are both methyl, a key intermediate for duloxetine in high optical purity and a process for preparation thereof.

In another aspect the present invention provides a process for preparation of (±)-N,N-dimethyl-3-(1-naphthalenyloxy)-3-(2-thienyl)propanamine comprising racemization of (R)-N,N-dimethyl-3-(1-naphthalenyloxy)-3-(2-thienyl)propanamine by treatment with a base.

In another aspect the present invention provides a process for preparation of an acid addition salt of duloxetine, particularly duloxetine hydrochloride.

The aryloxypropanamine compounds like the compound of formula 1 and a process for preparation thereof (see Scheme I) are disclosed in U.S. Pat. Nos. 4,956,388 and 5,023,269 (product patent).

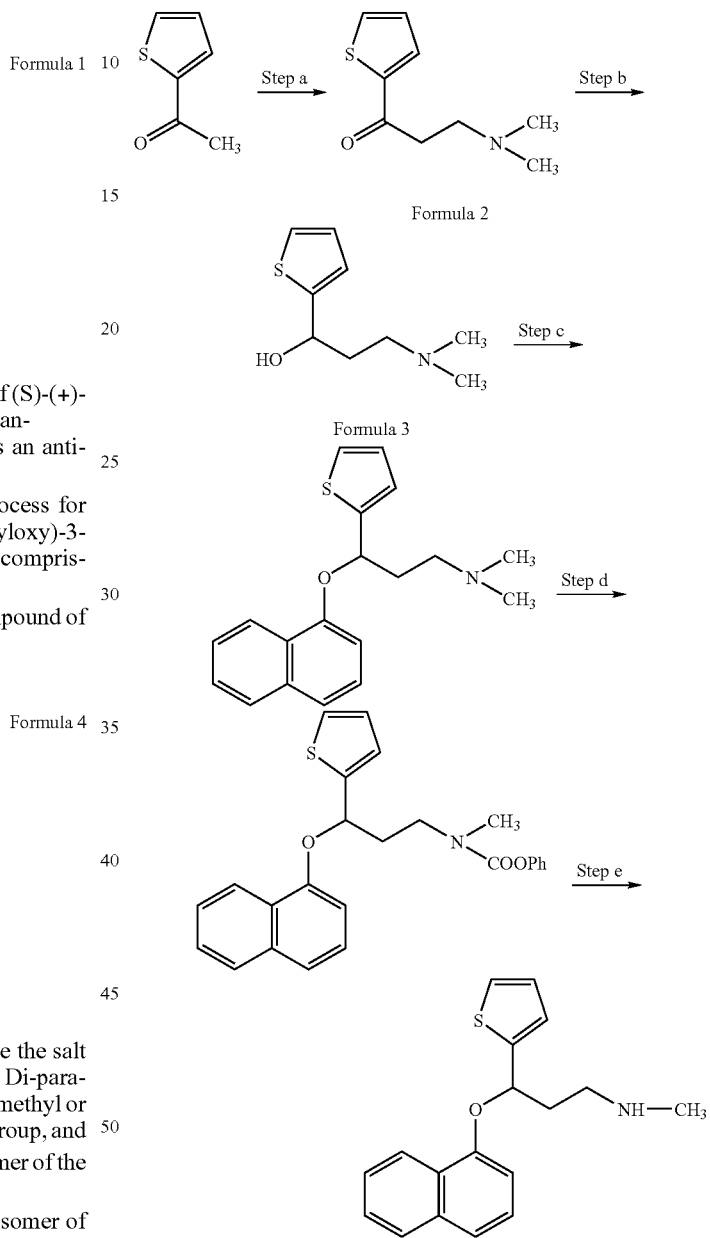

Scheme I

As depicted in Scheme I, in the product patent route 2-acetylthiophene is converted to 2-thienyl-2-dimethylaminoethyl ketone, a compound of formula 2 under Mannich reaction condition. The ketone of formula 2 is reduced to obtain the compound of formula 3, viz., N,N-dimethyl-3-hydroxy-3-(2-thienyl)-propanamine. The compound of formula 3 is converted to the aryl ether intermediate, namely, N,N-dimethyl-3-(1-naphthalenyloxy)-3-(2-thienyl)propanamine, by reacting with 1-fluoronaphthalene in presence of sodium hydride (NaH). The aryl ether intermediate is converted to the carbamate intermediate, a compound of formula 5, which after hydrolysis yields, N-methyl-3-(1-naphthalenyloxy)-3-(2-thienyl)propanamine, the hydrochloride salt of the S-isomer thereof, namely, (S)-(+)-N-methyl-3-(1-naphthalenyloxy)-3-(2-thienyl)propanamine known as duloxetine is of interest for use as an antidepressant.

Process for preparation of racemic aryloxypropanamine compounds has been exemplified in the product patent, however, the process for obtaining the optically active isomers is not detailed. The description provides that the optically active isomers may be prepared from optically active precursors or may be resolved from the racemic aryloxypropanamine compounds. These patents however, do not teach the method of obtaining the optically active precursor. For resolution of the aryloxypropanamine compounds, particularly useful resolving agents mentioned are, dibenzoyl-d- and -l-tartaric acid. However, we have found that dibenzoyl-d- and -l-tartaric acid is a poor resolving agent for N,N-dimethyl-3-(1-naphthalenyloxy)-3-(2-thienyl)propanamine.

The asymmetric synthesis of duloxetine involving use of lithium aluminum hydride complexed with a chiral ligand, to synthesize the compound of formula 3 in enantiomeric form has been discussed by Deeter et al in *Tetrahedron Letters*, 31(49), 7101-04, (1990). It is mentioned that this asymmetric synthesis typically provided duloxetine of >98% enantiomeric excess.

U.S. Pat. No. 5,362,886 (the '886 patent) teaches an improved process for preparation of duloxetine, wherein the racemic hydroxy compound of formula 3 is resolved by using optically active (S)-(+)-mandelic acid to obtain the S-isomer of compound of formula 3, namely, (S)-(−)-N,N-dimethyl-3-hydroxy-3-(2-thienyl)-propanamine. Thereafter 'Step c' has been carried out in presence of a potassium compound such as potassium benzoate or potassium acetate to obtain the S-isomer of the aryl ether intermediate, namely, (S)-(+)-N,N-dimethyl-3-(1-naphthalenyloxy)-3-(2-thienyl)propanamine. The S-isomer of this aryl ether intermediate, has been exemplified in Example 1 and isolated as phosphoric acid salt thereof with 91% enantiomeric excess (ee). In Example 2 duloxetine hydrochloride (duloxetine HCl) is prepared in ethyl acetate using concentrated HCl and by adding seed crystal.

Although '886 patent does not specifically disclose the ee of duloxetine HCl obtained in 'Preparation 2' from the phosphoric acid salt of the S-isomer of aryl ether intermediate having 91% ee, we have observed that it yields duloxetine HCl with an ee of about 98% with poor yield. To achieve further higher ee one needs to purify the S-isomer of aryl ether intermediate and then convert it to duloxetine HCl or purify duloxetien HCl repeatedly to improve its enantiomeric excess.

Moreover, when we repeated this example on higher scale, we have found it to be non-reproducible and also that dulxetine base would invariably undergo disintegration during treatment with concentrated HCl in ethyl acetate, as is evident from the low yield reported in the Example 2 of the '886 patent, of overall yield of about 27% only. Duloxetine has a 2-thienylmethyl-1-naphthyl ether component making it susceptible to cleavage under acidic conditions. Thus it would be advantageous to have a scaled-up, consistent, reproducible process for preparation of duloxetine HCl, free of undesired impurities.

As discussed hereinbefore it was important that one started with (S)-(+)-N,N-dimethyl-3-(1-naphthalenyloxy)-3-(2-thienyl)propanamine having higher enantiomeric purity so as to avoid multiple purifications either at intermediate stage or that of duloxetine HCl to achieve further higher enatiomeric purity of duloxetine HCl in high yields. Moreover use of aryl ether intermediate with ee of about 90% leads to optically impure final product.

Hence there is a need for developing a process, which consistently yields high purity aryl ether intermediate in terms of chemical and chiral purity. The present invention provides a more streamlined method for preparation of enantiomerically pure duloxetine by using readily available reagents.

In the prior art, the intermediate compound of formula 3 or formula 6 is resolved and then

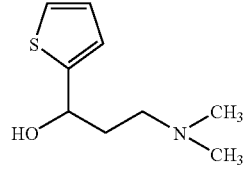

Formula 3

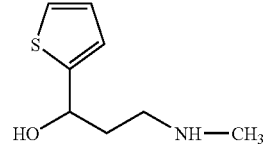

Formula 6 converted to (S)-isomer of the aryl ether intermediate. It means one needs to handle chiral intermediates at three stages in the process, Step c, Step d and Step e, and particularly one could envisage racemization during the formation of S-isomer of aryl ether intermediate wherein the compound could racemize in presence of a strong base like NaH, leading to lower enantiomeric purity of the intermediate.

PCT publication WO 03/070720 uses thiophene compounds containing a carbamate group for preparation of intermediate compound of formula 6. Examples 9 and 11 exemplify resolution of compound of formula 6 to obtain the S-enantiomer thereof by using L-(+)-mandelic acid as a resolving agent.

PCT publication WO 03/062219 teaches preparation of intermediate compound of formula 6 by subjecting the corresponding racemic compound to resolution with, (S)-(−)-2-Pyrrolidone-5-carboxylic acid or 2,3,4,6-Di-O-isopropylidene-2-keto-L-gulonic acid.

PCT publication WO 04/005307 teaches a process for preparation of enantiomerically enriched intermediate compound of formula 6 by subjecting the enantiomeric mixture thereof to resolution with 2,3,4,6-Di-O-isopropylidene-2-keto-L-gulonic acid.

PCT publication WO 04/056795 teaches resolution of final product, duloxetine using di-p-toluyl tartaric acid. A resolution of the final product is not an economical option, unless the chiral center is being formed only at the final synthetic step, which is not the case for duloxetine.

The prior art processes are able to provide duloxetine in about 98% enantiomeric excess. None of the prior art processes teach resolution of the aryl ether intermediate compounds of formula 4.

The present invention provides for resolution of the aryl ether intermediate, like N,N-dimethyl-3-(1-naphthalenyloxy)-3-(2-thienyl)propanamine. By this strategy, the risk of racemization of enantiomeric N,N-dimethyl-3-(1-naphthalenyloxy)-3-(2-thienyl)propanamine, which is present as step c needs to be carried out in presence of a base, is obviated, since racemic compound of formula 3 would be used to form racemic N,N-dimethyl-3-(1-naphthalenyloxy)-3-(2-thienyl)propanamine, which would be further resolved by the process of the present invention.

The present invention provides for use of Di-p-toluloyl tartaric acid (referred to as DPTTA herein) as an effective resolution agent for obtaining a compound of formula 4,

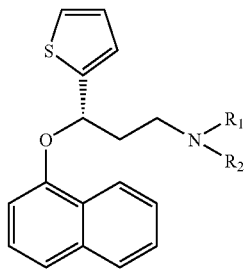

Formula 4 wherein $R_1$ and $R_2$ both are methyl or $R_1$ is methyl and $R_2$ is benzyl or substituted benzyl group in an enantiomerically enriched form, with optical purity of greater than 99%.

The resolution process of the present invention obviates the need of processing the optically active compound of formula 3 to obtain optically active aryl ether intermediate in presence of a hazardous and highly reactive base like NaH, which could lead to potential problems of racemization. Further, it provides a convenient alternative to use of unnatural derivatives of sugar like 2,3,4,6-Di-O-isopropylidene-2-keto-L-gulonic acid as resolving agent, which itself could be sensitive to moisture and acidic conditions.

In our experience, it was observed that optically active resolving agents routinely used on commercial scale such as tartaric acid, mandelic acid, camphor sulphonic acid etc did not work to resolve N,N-dimethyl-3-(1-naphthalenyloxy)-3-(2-thienyl)propanamine. Also, optically active dibenzoyl-tartaric acids were ineffective for resolution of this compound.

Di-para-toluoyl-L-tartaric acid works as an efficient resolving agent for preparation of (S)-isomer of compound of formula 4, for example, (S)-(+)-N,N-dimethyl-3-(1-naphthalenyloxy)-3-(2-thienyl)propanamine. The R-isomer enriched mother liquor containing (R)-(−)-N,N-dimethyl-3-(1-naphthalenyloxy)-3-(2-thienyl)propanamine can be racemized to obtain (±)-N,N-dimethyl-3-(1-naphthalenyloxy)-3-(2-thienyl)propanamine by treatment with a base, which can be further recycled and subjected to resolution process with DPTTA, thereby increasing the yield of desired enantiomer, (S)-(+)-N,N-dimethyl-3-(1-naphthalenyloxy)-3-(2-thienyl)propanamine.

For the compound of formula 4, $R_1$ and $R_2$ both are methyl or $R_1$ is methyl and $R_2$ is benzyl or substituted benzyl group. Examples of substituted benzyl group are those where phenyl ring of the benzyl group is substituted with one or more halogen, alkoxy or haloalkoxy group such as —$OCF_3$ group and the like, alkoxy or haloalkoxy preferably containing C1 to C5 carbon atoms.

For obtaining the other isomer of the compound of formula 4 for example, (R)-(−)-N,N-dimethyl-3-(1-naphthalenyloxy)-3-(2-thienyl)propanamine, Di-para-toluoyl-D-tartaric acid can be used as a resolving agent.

As in the present invention, the aryl ether intermediate is prepared in racemic form from racemic compound of formula 3, any base like potassium tert-butoxide, sodium methoxide, sodium hydroxide can be used for the conversion as the need to maintain the chirality in this step is obviated.

SUMMARY OF THE PRESENT INVENTION

In one aspect the present invention provides a process for preparation of (S)-isomer of compound of formula 4,

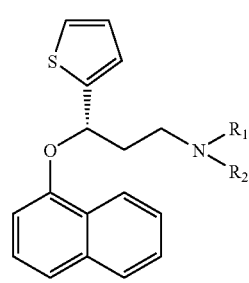

Formula 4 wherein $R_1$ and $R_2$ both are methyl or $R_1$ is methyl and $R_2$ is benzyl or substituted benzyl group, comprising the steps of
a) reacting a mixture of R and S enantiomers of compound of formula 4 with Di-para-toluoyl-L-tartaric acid to precipitate the salt of (S)-isomer of the compound of formula 4 with Di-para-toluoyl-L-tartaric acid; and
b) converting the said precipitated salt to the (S)-isomer of the compound of formula 4.

The present invention provides (S)-(+)-N,N-dimethyl-3-(1-naphthalenyloxy)-3-(2-thienyl)propanamine with greater than 98% enantiomeric excess, (S)-(+)-N-methyl-3-(1-naphthalenyloxy)-3-(2-thienyl)propanamine hydrochloride with greater than 99% enantiomeric excess and crude (S)-(+)-N-methyl-3-(1-naphthalenyloxy)-3-(2-thienyl) propanamine hydrochloride with greater than 99% enantiomeric excess.

In one aspect the present invention provides efficient resolution process for preparation of compound of formula 4 in desired isomeric form. In another aspect the present invention provides racemization process for converting the undesired isomer into racemic form, which can then be recycled to get increased yield of the desired isomer of compound of formula 4.

The present invention provides a process for preparation of (±)-N,N-dimethyl-3-(1-naphthalenyloxy)-3-(2-thienyl)propanamine, comprising racemization of (R)-N,N-dimethyl-3-(1-naphthalenyloxy)-3-(2-thienyl)propanamine by treatment with a base.

The present invention also provides a process for preparation of an acid addition salt of (S)-(+)-N-methyl-3-(1-naphthalenyloxy)-3-(2-thienyl)propanamine, a compound of formula 1A,

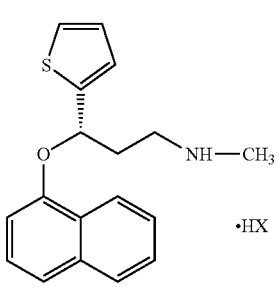

Formula 1A comprising reacting a compound of formula 1 in the form of free base with a compound represented by formula BHX in a protic solvent, wherein B represents a base and HX represents an acid.

DETAILED DESCRIPTION OF THE INVENTION

In one aspect the present invention provides efficient resolution process for preparation of compound of formula 4 in desired enantiomeric form using DPTTA.

The compound of formula 4 (wherein $R_1$ and $R_2$ both are methyl), namely, (S)-(+)-N,N-dimethyl-3-(1-naphthalenyloxy)-3-(2-thienyl)propanamine prepared according to the process of the present invention, can be converted to (S)-(+)-N-methyl-3-(1-naphthalenyloxy)-3-(2-thienyl)propanamine, a compound of formula 1 and optionally further converted to a pharmaceutically acceptable salt thereof, particularly the HCl salt thereof.

The compound of formula 4, wherein $R_1$ and $R_2$ both are methyl can be prepared by known processes as depicted in scheme 1.

The compound of formula 4, wherein $R_1$ is methyl and $R_2$ is benzyl or substituted benzyl can be prepared starting from 2-acetylthiophene, resolved to obtain the (S)-isomer thereof by reacting with Di-para-toluoyl-L-tartaric acid. The resultant (S)-isomer compound of formula 4 can be isolated and converted to (S)-(+)-N-methyl-3-(1-naphthaleneoxy)-3-(2-thienyl)propanamine, a compound of formula 1 by subjecting to debenzylation reaction for example, by catalytic hydrogenation (outlined in Scheme II below).

The desired S-isomer of compound of formula 4, for example, (S)-(+)-N,N-dimethyl-3-(1-naphthalenyloxy)-3-(2-thienyl)propanamine can be obtained from its Di-para-toluloyl tartaric acid salt by treatment with any suitable organic or inorganic base, followed by the subsequent conversion steps leading to (S)-(+)-N-methyl-3-(1-naphthalenyloxy)-3-(2-thienyl)propanamine as known in the art via a carbamate formation. If required, the enantiomerically enriched Di-para-toluloyl-L-tartaric acid salt of the (S)-isomer of compound of formula 4 can be subjected to purification from a suitable solvent to obtain desired enantiomeric excess. (S)-(+)-N-methyl-3-(1-naphthalenyloxy)-3-(2-thienyl)propanamine can be converted to a hydrochloride salt thereof, if desired.

The process of the present invention provides (S)-(+)-N,N-dimethyl-3-(1-naphthalenyloxy)-3-(2-thienyl)propanamine with greater than 98% enantiomeric excess.

As used herein the term "ee" or "enantiomeric excess" refers to the percent by which one enantiomer, E1 is in excess in a mixture of both enantiomers (E1+E2), as calculated by the equation, $[(E1-E2)/(E1+E2)] \times 100\% = ee$.

The present invention also provides acid addition salt of (S)-N,N-dimethyl-3-(1-naphthalenyloxy)-3-(2-thienyl)propanamine with Di-para-toluoyl-L-tartaric acid and acid addition salt of (R)-N,N-dimethyl-3-(1-naphthalenyloxy)-3-(2-thienyl)propanamine with Di-para-toluoyl-D-tartaric acid.

In another aspect the present invention provides a process for preparation of (±)-N,N-dimethyl-3-(1-naphthalenyloxy)-3-(2-thienyl)propanamine comprising racemization of (R)-

Scheme II

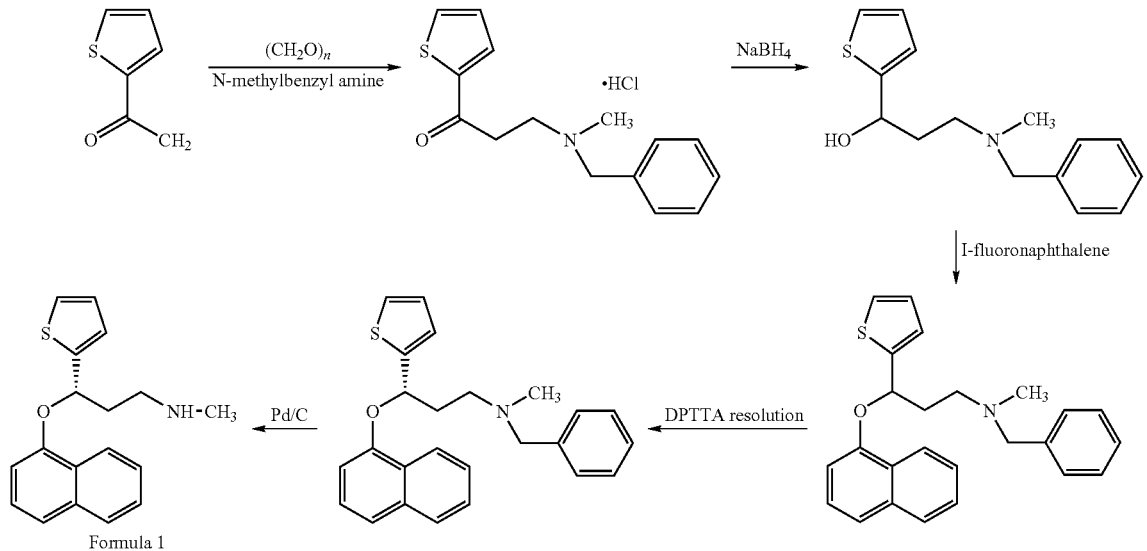

A suitable alcohol, ketone, nitrile, ester solvent may be used in the resolution process for preparation of desired isomeric compound of formula 4. Preferably an ester solvent like ethyl acetate.

The ratio of mixture of R and S enantiomers of the compound of formula 4 to the Di-para-toluoyl-L-tartaric acid is preferably from about 1:0.4 to 1:1 mole/mole, more preferably 1:0.48 mole/mole. To accelerate crystallization the solution may be optionally seeded with crystal of the desired isomer.

N,N-dimethyl-3-(1-naphthalenyloxy)-3-(2-thienyl)propanamine by treatment with a base.

Any suitable organic base like an alkali metal alkoxide for example, potassium tert-butoxide and the like or inorganic base like alkali or alkaline earth metal salts, for example, sodium hydroxide, potassium carbonate and the like in a suitable protic or aprotic solvents, preferably aprotic solvents like dimethylsulfoxide may be employed for carrying out the racemization of the unwanted (R)-isomer of N,N-dimethyl-3-(1-naphthalenyloxy)-3-(2-thienyl)propanamine, generated during resolution of the R and S enantiomers thereof. It is advantageous to perform the racemization reaction for converting the unwanted (R)-isomer in to the racemic forms thereof by treatment with potassium tert-butoxide in dimethyl sulfoxide solvent. Use of 0.5 equivalent of potassium tert-butoxide with respect to the R-isomer in the form of a free base, is sufficient to carry out the racemization of the unwanted (R)-isomer. The resultant racemized N,N-dimethyl-3-(1-naphthalenyloxy)-3-(2-thienyl)propanamine then can be recycled to generate the desired (S)-isomer thereof, thereby increasing the yield of the desired isomer.

The process of resolution of N,N-dimethyl-3-(1-naphthalenyloxy)-3-(2-thienyl)propanamine with Di-para-toluloyl-L-tartaric acid yields the aryl ether intermediate viz. (S)-(+)-N,N-dimethyl-3-(1-naphthalenyloxy)-3-(2-thienyl) propanamine a compound of formula 4 in high optical purity (greater than 98% ee) which can be further converted to the desired (S-enantiomer) duloxetine or its HCl salt with greater than 99% ee, preferably greater than 99.5% ee.

The process of the present invention employing Di-para-toluoyl-L-tartaric acid as a resolution agent for compound of formula 4, provides duloxetine HCl in greater than 99% ee, preferably greater than 99.5% ee.

In another aspect, the present invention in a preferred embodiment provides a process for preparation of hydrochloride salt of (S)-(+)-N-methyl-3-(1-naphthaleneoxy)-3-(2-thienyl)propanamine, a compound of formula 1, i.e. duloxetine hydrochloride (dulxetine HCl).

As discussed hereinbefore, we have observed that in preparation of duloxetine HCl, the use of mineral acid is highly detrimental. The present invention provides an alternative process.

The present invention provides a process for preparation of an acid addition salt of (S)-(+)-N-methyl-3-(1-naphthalenyloxy)-3-(2-thienyl)propanamine, a compound of formula Formula 1A

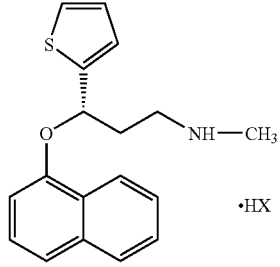

comprising reacting a compound of formula 1 in the form of free base with a compound represented by formula BHX in a protic solvent, wherein B represents a base and HX represents an acid.

Suitable acid addition salts of (S)-(+)-N-methyl-3-(1-naphthalenyloxy)-3-(2-thienyl)propanamine are salts of acids such as hydrochloric acid, hydrobromic acid, phosphoric acid, metaphosphoric acid, nitric acid and sulfuric acid.

In a preferred embodiment BHX is selected from a group consisting of ammonium chloride, anilinium chloride, trialkylamine hydrochloride, diarylamine hydrochloride and pyridine or substituted pyridine hydrochloride. The most preferred is ammonium chloride. The protic solvent may be any suitable solvent such as an alcohol, water or aqueous alcohol.

In preferred embodiment BHX is ammonium chloride and the protic solvent is an alcohol like methanol.

A salt like ammonium chloride provides a safe and efficient alternative to use of mineral acid in preparation of duloxetine HCl from a free base thereof, practically without formation of any undesired side-products. Apparently, duloxetine base having a stronger basic character is able to deprotonate ammonium chloride and in turn it gets protonated in presence of a protic solvent to afford duloxetine HCl in higher yields (about 50%) and practically no undesired side products. The duloxetine HCl thus obtained exhibits greater than 99.9% ee and assay greater than 99%.

Typically, the work-up of the reaction mixture containing the acid addition salt of (S)-(+)-N-methyl-3-(1-naphthalenyloxy)-3-(2-thienyl)propanamine can be carried out by isolating the acid addition salt by removing the reaction solvent, by filtration, centrifugation or concentration etc. The resultant product can be charcolized if desired, slurried in any suitable solvent if desired, and/or cooled to a lower temperature such as about 5 to about 10° C., isolated and optionally recrystallized from any suitable solvent. Alternately, after removing the reaction solvent, the resultant product can be dissolved into any suitable organic solvent, preferably water immiscible organic solvent, to form a solution and the solution may be washed with water. The separated organic layer may be charcolized if desired, dried, concentrated to remove the solvent. The resultant product if desired can be slurried in any suitable solvent, and/or cooled to a lower temperature such as about 5 to about 10° C., isolated and optionally recrystallized from any suitable solvent.

The present invention provides crude (S)-(+)-N-methyl-3-(1-naphthalenyloxy)-3-(2-thienyl)propanamine hydrochloride (duloxetine hydrochloride) with an enantiomeric purity greater than 99%, preferably greater than 99.5% ee.

Crude duloxetine hydrochloride is the product formed in the reaction mixture when duloxetine base is converted to dulxetine hydrochloride salt and/or isolated from the reaction mixture by any known technique in the art, for example, removal of reaction solvent by filtration, centrifugation, concentration, evaporation etc., slurrying in any suitable solvent and/or cooling to a temperature lower than the ambient conditions, without carrying out any further purification by way of recrystallization, any chromatographic purification or the like.

If desired, the crude duloxetine hydrochloride may be purified by any purification technique known in the art, for example crystallization from a suitable solvent. In a preferred embodiment the hydrochloride salt of (S)-(+)-N-methyl-3-(1-naphthalenyloxy)-3-(2-thienyl)propanamine is prepared by a process comprising, a) reacting a mixture of R and S enantiomers of N,N-dimethyl-3-(1-naphthalenyloxy)-3-(2-thienyl)propanamine with Di-para-toluoyl-L-tartaric acid to precipitate the salt of (S)-N,N-dimethyl-3-(1-naphthalenyloxy)-3-(2-thienyl)propanamine with Di-para-toluoyl-L-tartaric acid;

b) converting the said precipitated salt to (S)-(+)-N,N-dimethyl-3-(1-naphthalenyloxy)-3-(2-thienyl)propanamine;

c) further converting (S)-(+)-N,N-dimethyl-3-(1-naphthalenyloxy)-3-(2-thienyl)-propanamine to (S)-(+)-N-methyl-3-(1-naphthalenyloxy)-3-(2-thienyl)propanamine;

d) further treating (S)-(+)-N-methyl-3-(1-naphthalenyloxy)-3-(2-thienyl)propanamine in the form of free base with ammonium chloride in a protic solvent;

e) isolating (S)-(+)-N-methyl-3-(1-naphthalenyloxy)-3-(2-thienyl)propanamine hydrochloride salt and optionally further purifying.

The conversion of (S)-(+)-N,N-dimethyl-3-(1-naphthalenyloxy)-3-(2-thienyl)-propanamine to (S)-(+)-N-methyl-3-(1-naphthalenyloxy)-3-(2-thienyl)propanamine can be carried out by any process known in the art, for example, via a carbamate intermediate (as depicted in Scheme I), which on hydrolysis would provide (S)-(+)-N-methyl-3-(1-naphthalenyloxy)-3-(2-thienyl)propanamine, which can be converted to hydrochloride salt thereof by treatment with ammonium chloride in a protic solvent. The isolated (S)-(+)-N-methyl-3-(1-naphthalenyloxy)-3-(2-thienyl)propanamine hydrochloride salt if desired can be purified by any crystallization technique, known in the art.

In prior art duloxetine HCl has been prepared from duloxetine base by treatment with HCl in ethyl acetate solvent. As discussed herein, when we repeated this example on higher scale, we have found it to be non-reproducible and also that dulxetine base would invariably undergo decomposition during treatment with con HCl in ethyl acetate, as is evident from the low yield reported in the Example 2 of the '886 patent, of overall yield of about 27% only. Duloxetine has a 2-thienyl-methyl-1-naphthyl ether component making it susceptible to cleavage under acidic conditions. The miscibility of ethyl acetate in water being such that the excess HCl present in the reaction system remains in contact with duloxetine thereby inducing the formation of undesired side-products and lowering the yield of duloxetine.

We further report a novel process for preparation of acid addition salt of duloxetine using a mineral acid in a biphasic system. Particularly of interest is duloxeine HCl.

The present invention provides a process for preparation of hydrochloride salt of (S)-(+)-N-methyl-3-(1-naphthalenyloxy)-3-(2-thienyl)propanamine, a compound of formula 1,

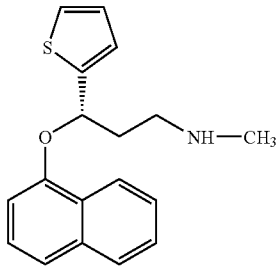

Formula 1 comprising treating a compound of formula 1 in the form of free base with HCl in a biphasic system consisting of aqueous phase and water immiscible organic solvent.

The advantages of the process involving use of a biphasic system over prior art system is that excess HCl would remain in the aqueous phase whereas duloxetine would be in organic phase thereby contact of excess HCl that may be present in the system with the duloxetine would be avoided. Thus the possibility of degradation of dulxetine in presence of HCl is reduced. The water immiscible organic solvent for example, dichloromethane being practically immiscible with water unlike ethyl acetate, is advantageously used in the biphasic system of the present invention for preparation of duloxetine HCl. Another practical advantage is that duloxetine HCl can be prepared conveniently at ambient conditions using the biphasic system of the process of the present invention.

Examples of the water immiscible organic solvents useful for the biphasic system are chlorinated hydrocarbons like dichloromethane, dichloroethane; aromatic hydrocarbons like toluene, xylene; cyclic and acyclic hydrocarbons like hexane, heptane, cyclohexane, petroleum ether fractions, ethers like diethylether. The preferred being chlorinated hydrocarbons, more preferably dichloromethane.

Typically the work-up of the reaction mixture containing the acid addition salt of (S)-(+)-N-methyl-3-(1-naphthalenyloxy)-3-(2-thienyl)propanamine can be carried out by isolating the acid addition salt from the water immiscible organic solvent The separated organic layer may be charcolized if desired, dried, concentrated to remove the solvent. The resultant product if desired can be slurried in any suitable solvent, and/or cooled to a lower temperature such as about 5 to about 10° C., isolated and optionally recrystallized from any suitable solvent.

In another preferred embodiment the hydrochloride salt of (S)-(+)-N-methyl-3-(1-naphthalenyloxy)-3-(2-thienyl)propanamine is prepared by a process comprising, a) reacting a mixture of R and S enantiomers of N,N-dimethyl-3-(1-naphthalenyloxy)-3-(2-thienyl)propanamine with Di-para-toluoyl-L-tartaric acid to precipitate the salt of (S)-N,N-dimethyl-3-(1-naphthalenyloxy)-3-(2-thienyl)propanamine with Di-para-toluoyl-L-tartaric acid;

b) converting the said precipitated salt to (S)-(+)-N,N-dimethyl-3-(1-naphthalenyloxy)-3-(2-thienyl)propanamine;

c) further converting (S)-(+)-N,N-dimethyl-3-(1-naphthalenyloxy)-3-(2-thienyl)-propanamine to (S)-(+)-N-methyl-3-(1-naphthalenyloxy)-3-(2-thienyl)propanamine;

d) further treating (S)-(+)-N-methyl-3-(1-naphthalenyloxy)-3-(2-thienyl)propanamine in the form of free base with HCl in a biphasic system consisting of aqueous phase and water immiscible organic solvent;

e) isolating (S)-(+)-N-methyl-3-(1-naphthalenyloxy)-3-(2-thienyl)propanamine hydrochloride salt and optionally further purifying.

The following examples are given by way of illustration only and not to be construed as limiting.

EXAMPLES

Example 1

Preparation of (S)-(+)-N,N-dimethyl-3-(1-naphthaleneoxy)-3-(2-thienyl)propanamine To 120 ml ethyl acetate is added 10 g (0.032 moles) of racemic N,N-Dimethyl-3-(1-naphthalenyloxy)-3-(2-thienyl)propanamine, followed by 5.95 g (0.015 moles) of Di-para-toluoyl-L-tartaric acid at 25° C.-28° C. The resultant clear solution is stirred at room temperature for about 2-3 hrs so as to crystallise the acid addition salt of the desired enantiomer of N,N-dimethyl-3-(1-naphthalenyloxy)-3-(2-thienyl)-propanamine. The product is filtered, washed with 100 ml ethyl acetate and dried at 60-70° C. Yield: 7.8 g, about 98% ee.

Example 2

Preparation of (S)-(+)-N-methyl-3-(1-naphthaleneoxy)-3-(2-thienyl)propanamine free base from Di-para-toluoyl-L-tartarate salt of (S)-(+)-N,N-dimethyl-3-(1-naphthaleneoxy)-3-(2-thienyl)propanamine To (777 ml) of DM water is added Di-para-toluoyl-L-tartarate salt of (S)-(+)-N,N-dimethyl-3-(1-naphthaleneoxy)-3-(2-thienyl)propanamine (111 gm) at 25-30° C., toluene (300 ml) is added, stirred for about 30 minutes, followed by addition of ammonia solution (about 25%, 100 ml) to the pH of about 9. The layers are separated, and aqueous layer is extracted with toluene (300 ml). The layers are separated and the aqueous layer is extracted with toluene (200 ml). The combined toluene extract is washed with water (2×100 ml)

and aqueous NaCl (10%), dried over sodium sulfate. About 100 ml toluene is distilled out under vacuum at 60-65° C. and then cooled to 40-45° C. Toluene (100 ml) is added, followed by addition of diisopropylethylamine (2 ml) and the reaction mixture is raised to 60-65° C., phenylchloroformate (31.2 gm) is added dropwise over about 30 minutes, then temperature is raised to 70-75° C. and maintained for 6 hours. The reaction mixture is cooled to 35-40° C. and worked up by treatment with aq NaHCO$_3$, HCl acid (1.0N), again with NaHCO$_3$ solution, followed by water and NaCl solution and dried over sodium sulfate. Toluene is distilled out under vacuum at 55-60° C. and residual mass is degassed under high vacuum (70 gm).

To the above residual mass, dimethylsulfoxide (360 ml) is added and heated to 40° C., followed by addition of NaOH flakes (20 gm) and water (60 ml). The temperature is gradually raised to 85-90° C. and stirred for 18 hours. The reaction mixture is cooled to 20-25° C. and quenched by adding water (650 ml) under stirring. The pH is adjusted to 5.5-6 by adding aq acetic acid (50%, about 80 ml) under stirring at 25-30° C. and stirred for 10-15 minutes. The reaction mixture is filtered thro hyflo, washed with hexane (210 ml). The product enriched aqueous layer is basified by adding slowly aq NaOH (25%) to pH of about 10.5 at 25-30° C. It is extracted with ethyl acetate (2×300 ml), the combined ethyl acetate layer is washed with water, dried, concentrated. The residual mass is degassed under high vacuum at 45-50° C. for 1 hour to obtain (S)-(+)-N-methyl-3-(1-naphthaleneoxy)-3-(2-thienyl)propanamine free base (38 gm), about 98% ee.

Example 3

Preparation of Duloxetine HCl Salt from (S)-(+)-N-methyl-3-(1-naphthaleneoxy)-3-(2-thienyl)propanamine Free Base To (S)-(+)-N-methyl-3-(1-naphthaleneoxy)-3-(2-thienyl) propanamine free base (65 gm) prepared as above, methanol (520 ml) is added under stirring. To the clear solution at 20-25° C., ammonium chloride (12.3 gm) is added under stirring. The reaction mixture is stirred at 20-25° C. for 1.5 hours. The solution is heated to 40-45° C. and methanol is distilled out under vacuum, residue is degassed. Isopropanol (520 ml) is added to it and charcolized at 40-45° C., filtered through Hyflo bed. The solvent is distilled out completely at 40-45° C. under vacuum. To the residue, acetone (650 ml) is added under stirring, cooled to 20-25° C., the slurry is stirred for 30 minutes. Then it is heated to 50-55° C. to dissolve. The clear solution is gradually cooled to 5-10° C. and maintained for 1-2 hours. The product is filtered and washed with acetone (100 ml), dried in air oven at 65-70° C. for 2-3 hours.

To duloxetine HCl obtained above, isopropanol (600 ml) is added under stirring and heated to 60° C. to get a clear solution, which is gradually cooled to 5-10° C. The solid is filtered and washed with acetone and dried at 60° C. to obtain pure duloxetine HCl (37 gm, 100% ee).

Preparation of Duloxetine HCl Salt from (S)-(+)-N-methyl-3-(1-naphthaleneoxy)-3-(2-thienyl)propanamine Free Base: Exemplifies Preparation of Pure Duloxetine HCl without Crystallization of the Salt To (S)-(+)-N-methyl-3-(1-naphthaleneoxy)-3-(2-thienyl) propanamine free base (65 gm) prepared as above, methanol (520 ml) is added under stirring. To the clear solution at 20-25° C., ammonium chloride (12.3 gm) is added under stirring. The reaction mixture is stirred at 20-25° C. for 1.5 hours. The solution is heated to 40-45° C. and methanol is distilled out under vacuum, residue is degassed. To the residue, dichloromethane (650 ml) is added under stirring, at 25-30° C. and the clear solution is stirred for 30 minutes. Then dichloromethane layer is washed with D.M Water (2×130 ml). Organic layer (dichloromethane layer) is charcoalised at 25-30° C., filtered through Hyflo bed and dried over sodium sulfate. Dichloromethane is distilled out under vacuum at 40-45° C. and residual mass is degassed under vacuum. Acetone (195 ml) is added to the residual mass at 25-30° C. to get a slurry and the resultant slurry is gradually cooled to 5-10° C. and maintained for 1-2 hours. The product is filtered and washed with acetone (100 ml), dried in air oven at 65-70° C. for 2-3 hours to obtain pure duloxetine HCl (35 g, 100% ee).

Example 4

Preparation of (±)-N,N-dimethyl-3-(1-naphthaleneoxy)-3-(2-thienyl)propanamine Oxalate Salt by Racemization of the (R)-N,N-dimethyl-3-(1-naphthaleneoxy)-3-(2-thienyl)propanamine The ethyl acetate filtrate containing the unwanted (R)-isomer as a major component generated during resolution of (±)-N,N-Dimethyl-3-(1-naphthalenyloxy)-3-(2-thienyl)propanamine in a similar manner as in Example 1 is subjected to racemization as below.

To the ethyl acetate filtrate (~100 ml) containing (R)-N,N-Dimethyl-3-(1-naphthalenyloxy)-3-(2-thienyl)propanamine, water (300 ml) is added and stirred. The reaction mixture is basified to pH of 8.5-10 by addition of aqueous ammonia solution (~20 ml, ~23%) at 25-30° C. and stirred for 15-20 minutes. The layers are separated and the aqueous layer is extracted with ethyl acetate (100 ml). The combined product enriched organic layers are washed with water (50 ml), aqueous sodium chloride solution (50 ml, ~15% w/v) and dried and the solvent distilled out to under vacuum and degassed.

To the residual mass (100 gm) obtained, dimethyl sulfoxide (400 ml) is added and stirred at 25-30° C., cooled to 15-20° C. and slowly powdered potassium tert-butoxide (18 gm) is added and the suspension is stirred for about 20 minutes at 20-25° C. The reaction mixture is gradually heated to about 80° C. and maintained under stirring for 4.5 to 5 hours. It is cooled to about 25° C. and water (1200 ml) is added and stirred for 15 minutes. The reaction mixture is extracted with ethyl acetate (2×400 ml). The product enriched ethyl acetate layers are washed with water (200 ml) and 10% aqueous sodium chloride solution (200 ml), dried. To the product enriched ethyl acetate solution oxalic acid (45 gm) and methanol (100 ml) are added under stirring at 20-25° C. The slurry is cooled to 15-20°c and maintained for 1 to 2 hours. The resultant product is filtered and washed with ethyl acetate (2×50 ml) and suck dried under vacuum (80 gm).

The invention claimed is:

1. A process for preparation of (S)-isomer of compound of formula 4,

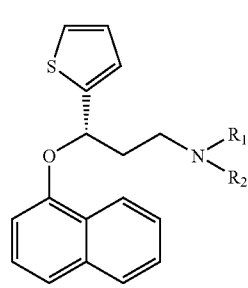

Formula 4 wherein R₁ and R₂ both are methyl or R₁ is methyl and R₂ is benzyl or substituted benzyl group, comprising the steps of
  a) reacting a mixture of R and S enantiomers of compound of formula 4 with Di-para-toluoyl-L-tartaric acid in ethyl acetate to precipitate the salt of (S)-isomer of the compound of formula 4 with Di-para-toluoyl-L-tartaric acid; and
  b) converting the said precipitated salt to the (S)-isomer of the compound of formula 4.

2. A process for the preparation of an acid addition salt of (S)-(+)-N-methyl-3-(1-naphthalenyloxy)-3-(2-thienyl)propanamine, a compound of formula 1A,

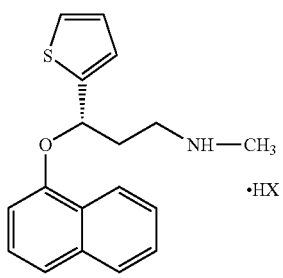

Formula 1A comprising the steps of:
  a) reacting a mixture of R and S enantiomers of N,N-dimethyl-3-(1-naphthalenyloxy)-3-(2-thienyl)propanamine with Di-para-toluoyl-L-tartaric acid in ethyl acetate to precipitate the salt of (S)-N,N-dimethyl-3-(1-naphthalenyloxy)-3-(2-thienyl)propanamine with Di-para-toluoyl-L-tartaric acid; and
  b) converting the said precipitated salt to (S)-(+)-N,N-dimethyl-3-(1-naphthalenyloxy)-3-(2-thienyl)propanamine;
  c) converting the (S)-(+)-N,N-dimethyl-3-(1-naphthalenyloxy)-3-(2-thienyl)propanamine to (S)-(+)-N-methyl-3-(1-naphthalenyloxy)-3-(2-thienyl)propanamime, a compound of formula 1

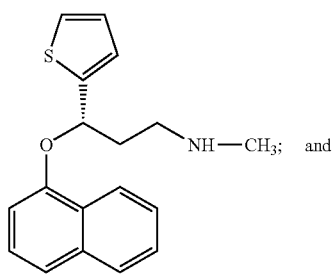

Formula 1 d) reacting the compound of formula 1 in the form of free base with a compound represented by formula BHX in a protic solvent, wherein B represents a base and HX represents an acid.

3. The process as claimed in claim 2, wherein (S)-(+)-N,N-dimethyl-3-(1-naphthalenyloxy)-3-(2-thienyl)propanamine is obtained with greater than 98% enantiomeric excess.

4. The process as claimed in claim 2, wherein (S)-(+)-N-methyl-3-(1-naphthalenyl-oxy)-3-(2-thienyl)propanamine is obtained with greater than 99% enantiomeric excess.

5. The process as claimed in claim 2, wherein the acid addition salt is hydrochloride salt.

6. The process as claimed in claim 2, wherein BHX is selected from a group consisting of ammonium chloride, anilinium chloride, trialkylamine hydrochloride, diarylamine hydrochloride and pyridine or substituted pyridine hydrochloride.

7. The process as claimed in claim 6, wherein BHX is ammonium chloride and the protic solvent is methanol.

8. A process for the preparation of (±)-N,N-dimethyl-3-(1-naphthalenyloxy)-3-(2-thienyl)propanamine, comprising racemization of (R)-N,N-dimethyl-3-(1-naphthalenyloxy)-3-(2-thienyl)propanamine by treatment with a base.

9. The process as claimed in claim 8, wherein said racemization is carried out by treatment with potassium tert-butoxide in dimethylsulfoxide.

10. A compound (S)-(+)-N,N-dimethyl-3-(1-naphthalenyloxy)-3-(2-thienyl)propanamine having greater than 98% enantiomeric excess.

11. A crude compound (S)-(+)-N-methyl-3-(1-naphthalenyloxy)-3-(2-thienyl)propanamine hydrochloride having greater than 99% enantiomeric excess.

12. A process for the preparation of an acid addition salt of (S)-(+)-N-methyl-3-(1-naphthalenyloxy)-3-(2-thienyl)propanamine, a compound of formula 1A,

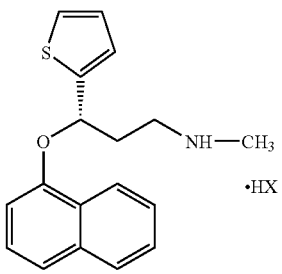

Formula 1A comprising the steps of:
  a) reacting a mixture of R and S enantiomers of N,N-dimethyl-3-(1-naphthalenyloxy)-3-(2-thienyl)propanamine with Di-para-toluoyl-L-tartaric acid in ethyl acetate to precipitate the salt of (S)-N,N-dimethyl-3-(1-aphthalenyloxy)-3-(2-thienyl)propanamine with Di-para-toluoyl-L-tartaric acid; and
  b) converting the said precipitated salt to (S)-(+)-N-N-dimethyl-3-(1-naphthalenyloxy)-3-(2-thienyl)propanamine
  c) converting the (S)-(+)-N,N-dimethyl-3-(1-naphthalenyloxy)-3-(2-thienyl)propanamine to (S)-(+)-N-methyl-3-(1-naphthalenyloxy)-3-(2-thienyl)propanamine, a compound of formula 1

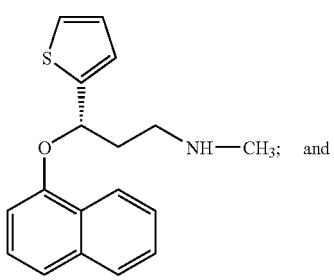

Formula 1 d) treating the compound of formula 1 with HCl in a biphasic system consisting of aqueous phase and water immiscible organic solvent.

* * * * *